US00RE38749E

(19) United States
(12) Reissued Patent
Dardik

(10) Patent Number: US RE38,749 E
(45) Date of Reissued Patent: Jun. 28, 2005

(54) CHRONOTHERAPY EXERCISE TECHNIQUE

(75) Inventor: Irving I. Dardik, Califon, NJ (US)

(73) Assignee: Lifewaves International, Inc., Califon, NJ (US)

(21) Appl. No.: 09/669,988

(22) Filed: Sep. 15, 2000

Related U.S. Patent Documents

Reissue of:
(64) Patent No.: 5,810,737
Issued: Sep. 22, 1998
Appl. No.: 08/944,862
Filed: Oct. 6, 1997

U.S. Applications:

(63) Continuation-in-part of application No. 08/151,508, filed on Nov. 12, 1993, now Pat. No. 5,752,521.

(51) Int. Cl.[7] ..... A61B 5/02
(52) U.S. Cl. ..... 600/500; 482/9
(58) Field of Search ..... 600/500–503

(56) References Cited

U.S. PATENT DOCUMENTS

| | | | | |
|---|---|---|---|---|
| 3,518,985 | A | 7/1970 | Quinton | 128/707 |
| 3,675,640 | A | 7/1972 | Gatts | 272/DIG. 6 |
| 3,802,698 | A | 4/1974 | Burian et al. | 272/57 R |
| 3,978,849 | A | 9/1976 | Geneen | 128/2.05 T |
| 4,278,095 | A | 7/1981 | Lapeyre | 128/689 |
| 4,301,808 | A | 11/1981 | Taus | 128/687 |
| 4,358,105 | A | 11/1982 | Sweeney, Jr. | 272/73 |
| 4,367,752 | A | 1/1983 | Jimenez et al. | 128/689 |
| 4,425,921 | A | 1/1984 | Fujisaki et al. | 128/690 |
| 4,436,097 | A | 3/1984 | Cunningham | 128/707 |
| 4,566,456 | A | 1/1986 | Koning et al. | 128/419 |
| 4,613,129 | A | 9/1986 | Schroeder et al. | 272/73 |
| 4,622,980 | A | 11/1986 | Kunig | 128/704 |
| 4,683,891 | A | 8/1987 | Cornellier et al. | 128/630 |
| 4,719,920 | A | 1/1988 | Alt et al. | 128/419 |
| 4,788,983 | A | 12/1988 | Brink et al. | 128/734 |
| 4,807,639 | A | 2/1989 | Shimizu et al. | 128/690 |
| 4,867,442 | A | 9/1989 | Matthews | 272/93 |
| 4,883,063 | A | 11/1989 | Bernard et al. | 128/670 |
| 4,896,675 | A | 1/1990 | Ohsuga et al. | 128/671 |
| 4,938,228 | A | 7/1990 | Righter et al. | 128/690 |

(Continued)

FOREIGN PATENT DOCUMENTS

| | | |
|---|---|---|
| CA | 2091101 | 9/1993 |
| CN | 1095917 | 12/1994 |
| DE | 3045923 | 9/1981 |

(Continued)

OTHER PUBLICATIONS

Acker J.E., Jr. et al., "Assessing psychological problems from a cardiologist's point of view," (Abstract) *Advances in Cardiology*, 31 at 218–22 (1982).

Ades P.A. et al., "Hypertension, exercise and beta–adrenergic blockade," (Abstract) *Annals of Internal Medicine*, 109 (8) at 629–34 (Oct. 15, 1988).

Aizaki T. et al., "Development of an ambulatory 24–hour recording device of electrocardiogram and exercise intensity and its analytic system," (Abstract) *Japan Journal of Med. Electron. Biol. Eng.* 32/2 at 83–90 (1994).

(Continued)

*Primary Examiner*—John P. Lacyk
(74) *Attorney, Agent, or Firm*—Fish and Neave LLP; Joel Weiss; Jeffrey C. Aldridge

(57) ABSTRACT

A chronotherapy exercise technique for treating a patient whose abnormal condition, regardless of its nature or origin, is reflected by a heart rate variability (HRV) that is reduced and deviates from an HRV reflecting a normal condition. In this treatment, the patient in an exercise session undergoes a series of exercise-relaxation cycles in which during each cycle the pulse rate of the patient rises and then falls to generate a heart wave. To enhance the efficacy of the treatment, the heart waves generated in the course of an exercise session are synchronized in time with an internal wave produced by a biological clock, this activity functioning to expand the range of the biological wave and inducing the HRV to approach an HRV, which for the patient being treated reflects a normal condition.

33 Claims, 1 Drawing Sheet

U.S. PATENT DOCUMENTS

| | | | | |
|---|---|---|---|---|
| 5,007,430 | A | 4/1991 | Dardik | 128/696 |
| 5,163,439 | A | 11/1992 | Dardik | 128/696 |
| 5,267,568 | A | 12/1993 | Takara | 128/687 |
| 5,410,472 | A | 4/1995 | Anderson | 364/413.04 |
| 5,752,521 | A | 5/1998 | Dardik | 128/687 |

FOREIGN PATENT DOCUMENTS

| | | |
|---|---|---|
| DE | 3409792 | 9/1984 |
| DE | 3532620 | 3/1986 |
| DE | 5338958 | 5/1994 |
| EP | 5949 | 12/1979 |
| EP | 117330 | 9/1984 |
| EP | 172747 | 2/1986 |
| EP | 181067 | 5/1986 |
| EP | 419103 | 3/1991 |
| EP | 556702 | 8/1993 |
| FI | 8304152 | 5/1985 |
| FI | 8900776 | 8/1989 |
| FI | 9504300 | 3/1996 |
| FR | 2569158 | 2/1986 |
| FR | 2599616 | 12/1987 |
| GB | 2052051 | 1/1981 |
| GB | 2165352 | 4/1986 |
| GB | 2184361 | 6/1987 |
| GB | 2253706 | 9/1992 |
| GB | 2306659 | 5/1997 |
| JP | 07313474 | 12/1995 |
| WO | 85/00279 | 1/1985 |
| WO | 90/12538 | 11/1990 |
| WO | 93/14807 | 8/1993 |
| WO | 94/02904 | 2/1994 |
| WO | 97/22295 | 6/1997 |

OTHER PUBLICATIONS

Balogun J.A. et al., "Cardiovascular adjustments and perceived exertion during exercise on the BAPS board," (Abstract) *Disability and Rehabilitation*, 17 (8) at 430–6 (Nov.–Dec. 1995).

Belardinelli R. et al., "Exercise training improves left ventricular diastolic filling in patients with dilated cardiomyopathy. Clinical and prognostic implications," (Abstract) *Circulation*, 91 (11) at 2775–84 (Jun. 1, 1995).

Brusis O.A., "Rehabilitating coronary patients through exercise," (Abstract) *Postgraduate Medicine*, 44 (1) at p. 131–5 (Jul. 1968).

Bryniarski L. et al., "Effect of exercise rehabilitation on heart rate variability in hypertenxives after myocardial infarction," (Abstract) *Journal of Hypertension*, 15 (12 pt 2) at 1739–43 (Dec. 1997).

Calzolari A.M. et al., "Rehabilitation of children after total correction of tetralogy of Fallot," (Abstract) *International Journal of Cardiology*, 28 (2) at 151–8 (Aug. 1990).

Cambach W. et al., "The effects of a community–based pulmonary rehabilitation programme on exercise tolerance and quality of life: a randomized controlled trial," (Abstract) *European Respiratory Journal*, 10 (1) at 104–13 (Jan. 1997).

Cerny F.J., "Relative effects of bronchial drainage and exercise for in–hospital care of patients with cystic fibrosis," (Abstract) *Phys. Ther.* 69/80 at 633–639 (1989).

Claus J. et al., "Special aspects of physical traning during the rehabilitation stage of coronary patients," (Abstract) *Herz*, 16 (4) at 199–209 (Aug. 1991).

Cooney M.M. et al., "Hydraulic resistance exercise benefits cardiovascular fitness of spinal cord injured," (Abstract) *Medicine and Science in Sports and Exercise*, 18 (5) at 522–5 (Oct. 1986).

Crakes J.G. et al., "Endpoints of chronobiologic cardiovascular monitoring during pregnancy for planning exercise and assessing effects," (Abstract) *Progress in Clinical and Biological Research*, 341A at 605–14 Ref: 28 (1990).

Czernin J. et al., "Effect of short–term cardiovacular conditioning and low–fat diet on myocardial blood flow and flow reserve," (Abstract) *Circulation*, 92 (2) at 197–204 (Jul. 15, 1995).

Dardik Irving I., "The Great Law of the Universe," *Cycles* at 265–277 (Mar.–Apr. 1994).

Dardik Irving I., "The Law of Waves and the Invalidation of the Scientific Method," *Cycles*, vol. 45, No. 2 at 49–60 (Feb. 1995).

Dardik Irving I., "The Origin of Disease and Health, Heart Waves: The Single Solution to Heart Rate Variability and Ischemic Preconditioning," *Cycles*, vol. 46, No. 3 at 67–77 (Dec. 1996).

Dardik Irving I., "The Origin of Disease and Health, Heart Waves: The Single Solution to Heart Rate Variability and Ischemic Preconditioning," *Frontier Perspectives*, vol. 6, No. 2 at 18–32 (Spring/Summer, 1997).

Dardik Irving I., "Research proposals for studying mind–body interactions, Cardiocybernetics*: Relaxation through Exercise," *Advances, Journal of the Institute for the Advancement of Health*, vol. 8, No. 3 at 56–59 (Summer 1986).

De Vries H.A. et al., "Electromyographic comparison of single doses of execise and meprobamate as to effects on muscular relaxtion," (Abstract) *American Journal of Physical Medicine*, 51 (3) at 130–41 (Jun. 1972).

DiCarlo S. et al., "Hemodynamic and and energy cost responses to changes in arm exercise technique," (Abstract) *Physical Therapy*, 63 (10) at 1585–92 (Oct. 1983).

Estok P.J. et al., "Jogging: cardiovascular benefits and risks," (Abstract) *Nurse Practitioner*, 11 (5) at 21–8 (May 1986).

Ewart C.K. et al. "Usefulness of self–efficacy in predicting overexertion during programmed exercise in coronary artery disease," (Abstract) *American Journal of Cardiology*, 57 (8) at 557–61 (Mar. 1, 1986).

Fletcher G.F., "Rehabilitative exercise for the cardiac patient. Early phase," (Abstract) *Cardiology Clinics*, 11 (2) at 267–75 Ref: 20 (May 1993).

Fletcher G.F. et al., "Continuous ambulatory electrocardiographic monitoring. Use in cardiac exercise programs," (Abstract) *Chest*, 71 (1) at 27–32 (Jan. 1977).

Folgering H. et al., "Exercise limitations in patients with pulmonary diseases," (Abstract) *International Journal of Sports Medicine*, 15 (3) at 107–11 (Apr. 1994).

Freedman R. et al., "Biofeedback and progressive relaxation treatment of sleep–onset insomnia: a controlled, all–night investigation," (Abstract) *Biofeedback and Self Regulation*, 1 (3) at 253–71 Journal code: A15 (Sep. 1976).

Fujita Y. et al., "Relationship between age–adjusted heart rate and anaerobic threshold in estimating exercise intensity in diabetics," (Abstract) *Diabetes Res. Clin. Pract.*, 8/1 at 69–74 (1990).

Fulcher K.Y. et al., "Randomised controlled trial of graded exercise in patients with the chronic fatigue syndrome," (Abstract) *BMJ* (*Clinical Research Ed.*), 314 (7095) at 1647–52 (Jun. 7, 1997).

Garfinkel Alan et al., "Heart Rate Dynamics After Acute Cocaine Administration," *Journal of Cardiovascular Pharmacology*, vol. 19, No. 3 at 453–459 (1992).

Goldberg A.P. et al., "Therapeutic benefits of exercise training for hemodialysis patients," (Abstract) Kidney International Supplement, 16 at S303–9 (Dec. 1983).

Gordon N.F. et al., "Exercise and mild essential hypertension," (Abstract) *Primary Care; Clinics in Office Practice*, 18 (3) at 683–94 Ref: 60 (Sep. 1991).

Greer M. et al., "Physiological responses to low–intensity cardiac rehabilitation exercises," (Abstract) *Physical Therapy*, 60 (9) at 1146–51 (Sep. 1980).

Hertzeanu H.L. et al., "Ventricular arrhythmias in rehabilitated and nonrehabilitated post–myocardial infarction patients with left ventricular dysfunction," (Abstract) *American Journal of Cardiology*, 71 (1) at 24–7 (Jan. 1, 1993).

Hooker S.P. et al., "Physiologic effects of electrical stimulation leg cycle exercise training in spinal cord injured persons," (Abstract) *Archives of Physical Medicine and Rehabilitation*, 73 (5) at 470–6 (May 1992).

Hrushesky William J. M., "Timing is everything," *The Sciences*, at 32–37 (Jul./Aug. 1994).

Iwadare M. et al., "Exercise prescription for physical training in hypertensive patients," (Abstract) *Nippon Rinsho. Japanese Journal of Clinical Medicine*, 50 Suppl. at 160–7 (May 1992).

Jovanovic–Peterson L. et al., "Randomized trial of diet versus diet plus cardiovascular conditioning on glucose levels in gestational diabetes," (Abstract) *American Journal of Obstetrics and Gynecology*, 161 (2) at 415–9 (Aug. 1989).

Kamata H. et al., "Semi–supervised exercise using a step machine at home after myocardial infarction," (Abstract) *Journal of Cardiology*, 29 (1) at 23–8 (Jan. 1997).

Katoh J. et al., "Cardiorespiratory effects of weight reduction by exercise in middle–aged women with obesity," (Abstract) *Journal of International Medical Research*, 22 (3) at 160–4 (May–Jun. 1994).

Kellermann J.J., "Rationale of exercise therapy in patients with angina pectoris with normal and impaired ventricular function," (Abstract) *Chest. 101/5 Suppl.* at 322S–325S (1992).

King C.N. et al., "Exercise testing and prescription. Practical recommendations for sedentary," (Abstract) *Sports Medicine*, 21 (5) at 326–36 (May 1996).

Koch S.M., "Effect of passive range of motion on intracranial pressure in neurosurgical patients," (Abstract) *Journal of Critical Care*, 11 (4) at 176–9 (Dec. 1996).

Kohno M. et al., "Effects of exercise therapy on blood pressure and hormonal factors in subjects with borderline and mild hypertension," (Abstract) *Bull. Phys. Fitness Res. Inst.* –/72 at 81–86 (1989).

Leitch J.W. et al., "Randomized trial of a hospital–based exercise training program after acute myocardial infarction: cardiac autonomic effects," (Abstract) *Journal of the American College of Cardiology*, 29 (6) at 1263–8 (May 1997).

Malik Marek et al., "Heart Rate Variability: Standards of Measurement, Physiological Interpretation, and Clinical Use," *A.N.E.*, vol. 1, No. 2, Pt. 1, at 151–181 (Apr. 1996).

Malikov V.A. et al., "Selection of optimal training exercise and training schedule for patients with ischemic heart disease at the early periods after aortocoronary bypass," (Abstract) *Kardiologiia* 31 (7) at 17–20 (Jul. 1991).

Malpas et al., "Circadian Variation Of Heart Rate Variability," Cardiovascular Research, vol. 24, at 210–213 (1990).

Marcelino J. et al., "Assessment of a circuit of exercises through heart rate response," (Abstract) *International Journal of Cardiology*, 49 (2) at 153–8 (Apr. 1995).

Masuoka, Toshiharu, "A Clinical Study of Exercise Training after Reperfusion Therapy in Patients with Myocardial Infarction," (Abstract) *Abstracts For Hiroshima Daigaku Igaku Zasshi*, 43(3) at 149–160 (1995).

Maynard T., "Exercise: Part II. Translating the exercise prescription," (Abstract) *Diabetes Educator* 17 (5) at 384–95 Ref: 13 (Sep.–Oct. 1991).

Mead W.F., "Exercise rehabilitation after myocardial infarction," (Abstract) *American Family Physician*, 15 (3) at 121–5 (Mar. 1977).

Melton–Rogers S et al., "Cardiorespiratory responses of patients with rheumatoid arthritis during bicycle riding and running in water," (Abstract) *Physical Therapy*, 76 (10) at 1058–65 (Oct. 1996).

Mertens D.J. et al., "Exercise training for patients with chronic atrial fibrillation," (Abstract) *Journal of Cardiopulmonary Rehabilitation*, 16 (3) at 193–6 (May–Jun. 1996).

Meyer K. et al., "Resistance exercise in comparison to bicycle ergometry. A study into the suitability of resistance training in exercise therapy for coronary patients," (Abstract) *Z. Kardiol.*, 81/10 at 531–537 (1992).

Meyer K. et al., "Can the training of coronary patients be monitored by readily measurable parameters?," (Abstract) *Herz*, 16 (4) at 251–6 (Aug. 1991).

Mineo K. et al., "Graded exercise in three cases of heart rupture after acute myocardial infarction," (Abstract) *American Journal of Physical Medicine and Rehabilitation*, 74 (6) at 453–7 (Nov.–Dec. 1995).

Mink B.D., "Pulmonary concerns and the exercise prescription," (Abstract) *Clinics in Sports Medicine*, 10 (1) at 105–16 Ref: 33 (Jan. 1991).

Neubauer B. et al., "Analysis of heart rate variations in patients with multiple sclerosis," *Journal of Neurology, Neurosurgery, and Psychiatry*, 41 at 417–419 (1978).

Oldridge N.B., "Carotid palpation, coronary heart disease and exercise rehabilitation," (Abstract) *Medicine and Science in Sports and Exercise*, 13 (1) at 6–8 (1981).

Otsuka Kuniaki et al., "Circadian rhythmic fractal scaling of heart rate variability in health and coronary artery disease", *Clinical Cardiology*, 20 at 631–638 (1977).

Ramazanoglu Y.M. et al., "Cardiorespiratory response to physical conditioning in children with bronchial asthma," (Abstract) Pediatric Pulmonology, 1 (5) at 272–7 (Sep.–Oct. 1985).

Redlin Uwe et al., "Exercise and human circadian rhythms: What we know and what we need to know," *Chronobiology International*, 14(2) at 221–119 (1997).

Reilly K. et al., "Differences between a supervised and independent strength and conditioning program with chronic low back syndromes," (Abstract) *Journal of Occupational Medicine*, 31 (6) at 547–50 (Jun. 1989).

Rousch Wade, "Can resetting hormonal rhythms treat illness?", *Science*, 269 at p. 1220–21 (1995).

Samitz G., "Aerobic upper body exercise. An unused potential in exercise therapy," (Abstract) *Wien. Med. Wochenschr.*, 142/14 at 309–313 (1992).
Schechtman V.L., "Bynamic Analysis of Cardiac R–R Intervals in Normal Infacts Who Subsequently Succumbed to the Sudden Infant Death Syndrome," *Pediatric Research*, vol. 31, No. 6 at 606–612 (1992).
Schwartz Tony, "Making Waves. Can Dr. Irv Dardik's Radical Exercise Therapy Really Work Miracles," *New York* at 31–39 (Mar. 18, 1991).
Sparks K.E. et al., "Alternatives for cardiac rehabilitation patients unable to return to a hospital–based program," (Abstract) *Heart and Lung*, 22 (4) at 298–303 (Jul.–Aug. 1993).
Stephens R. et al., "Effects of self–monitored exercise on selected blood chemistry parameters of end–stage renal disease patients," (Abstract) *American Journal of Physical Medicine and Rehabilitation*, 70 (3) at 149–53 (Jun. 1991).
Stevens R. et al., "Comparison of supervised and unsupervised exercise training after coronary bypass surgery," (Abstract) *American Journal of Cardiology*, 53 (11) at 1524–8 (Jun. 1, 1984).
Tamiya N., "Study of physical fitness in children, and its application to pediatric clinics and sports medicine," (Abstract) *Hokkaido Igaku Zasshi. Hokkaido Journal of Medical Science*, 66 (6) at 849–67 (Nov. 1991).
Taniguchi K. et al., "Predischarge early exercise therapy in patients with acute myocardial infarction on the basis of anaerobic threshold (AT)," (Abstract) *Jpn. Circ. J.*, 54/11 at 1419–1425 (1990).
Todd I.C. et al., "Effect of exercise training on the total ischaemic burden: an assessment by 24 hour ambulatory electrocardiographic monitoring," (Abstract) *British Heart Journal*, 68 (6) at 560–6 (Dec. 1992).
Tsuji Hisako et al., "Reduced Heart Rate Variability and Mortality Risk in an Elderly Cohort, The Framingham Heart Study," *Circulation*, vol. 90, No. 2 at 878–883 (Aug. 1994).
Ueshima K. et al., "Management and evaluation of non–supervised home exercise program in a convalescent phase of acute myocardial infarction," (Abstract) *Japanese Circulation Journal*, 54 (11) at 1437–42 (Nov. 1990).
van Dixhoorn J. et al., "Physical training and relaxation therapy in cardiac rehabilitation assessed through a composite criterion for training outcome," (Abstract) *American Heart Journal*, 118 (3) at 545–52 (Sep. 1989).
Waddington J.L. et al., "Resting heartrate variability in man declines with age," *Experience*, 35 at 1197–1198 (1979).
Wheeler Timothy et al., "Cardiac Denervation in Diabetes," *British Medical Journal*, 4 at p. 584–586 (Dec. 8, 1973).
Williams L.R. et al., "Vascular rehabilitation: benefits of a structured exercise/risk modification program," (Abstract) *Journal of Vascular Surgery*, 14 (3) at 320–6 (Sep. 1991).
Williams M.A. et al., "Guidelines for exercise therapy of the elderly after myocardial infarction," (Abstract) *Eur. Heart J. 5, Supplement E* at 121–123 (1984).
Wolfe L.A. et al., "Prescription of aerobic exercise during pregnancy," (Abstract) *Sports Medicine*, 8 (5) at 273–301 Ref: 133 (Nov. 1989).
Wright N.C. et al., "Aerobic walking in slowly progressive neuromuscular disease: effect of a 12–week program," (Abstract) Archives of Physical Medicine and Rehabilitation, 77 (1) at 64–9 (Jan. 1996).

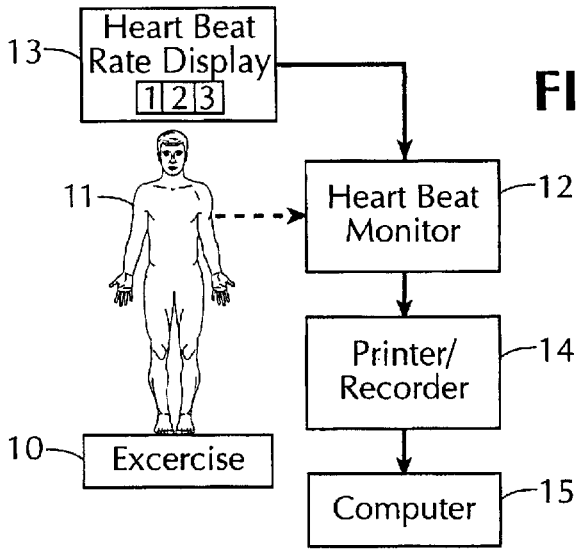
FIG. 1
FIG. 2
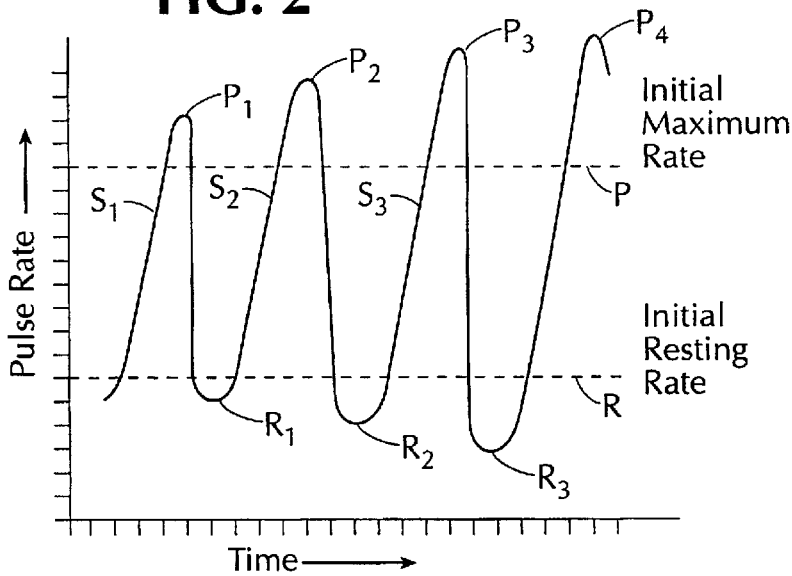
FIG. 3
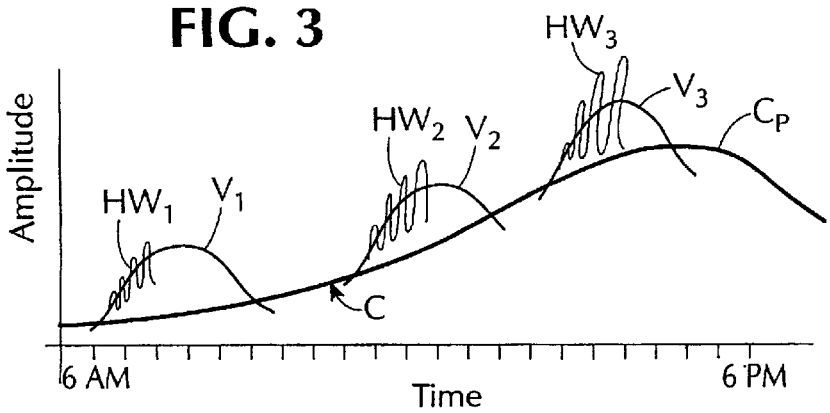

CHRONOTHERAPY EXERCISE TECHNIQUE

Matter enclosed in heavy brackets [ ] appears in the original patent but forms no part of this reissue specification; matter printed in italics indicates the additions made by reissue.

RELATED APPLICATION

This application is a continuation-in-part of our application Ser. No. 08/151,508 filed Nov. 12, 1993 U.S. Pat. No. 5,572,521 entitled "THERAPEUTIC EXERCISE TECHNIQUE," the entire disclosure of which is incorporated herein by reference.

BACKGROUND OF INVENTION

1. Field of Invention

This invention relates generally to a therapeutic exercise technique in which a patient suffering from an abnormal condition undergoes during an exercise session a series of exercise-relaxation cycles generating heart waves, and more particularly to a chronotherapy technique in which the heart waves generated in each exercise session are synchronized in time with an internal wave produced by a biological clock to enhance the efficacy of treatment.

2. Status of Prior Art

The human heart consists of two pumps having similar outputs, one pump sending blood through a pulmonary network, the other through the systemic network of the body. The human heart pumps the entire blood contents of the body through its chambers every minute. In mechanical terms, the heart exerts between 35–50 foot-pounds of pressure every minute. During strenuous exercise, it may exert as much as 500 foot-pounds.

A heart beat or pulse is one complete pulsation of the heart. A typical infant has a heart rate at rest of 130 beats per minute. This rate thereafter slows down so that in adulthood the rate at rest is about 70 beats per minute. When an increased demand is made upon the heart, the heart pulse rate quickens and the heart also pumps more blood with each beat, so that the heart output can be nearly doubled from its normal resting output.

Physical activity requires the expenditure of energy, and with exercise the heart pulse rate of a child may rise as high as 200 beats per minute, the rate dropping to about 80 when the child lies down. With aging, one experiences a progressive decline in the maximum heart pulse rate. In exercise physiology, the rule of thumb is that an individual's maximum heart rate is 220 minus his age. Hence for a 50 year old individual, his attainable maximum pulse rate is 220–50 which is 170 beats per minute.

My prior U.S. Pat. No. 5,007,430 discloses an exercise technique for inducing relaxation to counteract the adverse physiological and psychological effects of chronic stress on an individual. In this technique the individual being treated is coupled to a heart beat monitor and his heart beat is constantly monitored and displayed to him as he goes through a conditioning exercise session constituted by successive exercise-relaxation cycles running for a predetermined period.

In the course of each cycle, the individual while operating a stationary bicycle, a rowing machine or other exercise apparatus, is required to raise his level of exertion, as indicated by his perceived heart pulse rate, to a peak representing a predetermined safe upper limit, following which he must decrease his exertion until he reaches a lower limit at which a recovery-relaxation response takes place. The upper and lower limits are determined by the individual's existing capacity for exercise and defines his target heart rate zone.

My prior exercise technique whose purpose is to relieve mental stress is grounded on the premise that the exertion experienced in exercise and the recovery therefrom entail physiological and psychological processes that effectively corresponding to stress and relaxation.

The present state of medical knowledge with regard to chronic diseases is such that no single cause or cure therefor has yet to be found. Chronic diseases have been imputed to a multitude of factors, such as structural abnormalities, gene mutation and altered levels of chemicals, e.g. cholesterol, calcium, T-4 cells, etc. This is the current basis for biochemical testing of a patient's condition. Behavioral factors also come into play in producing such disorders as obesity, clinical depression and sleep abnormalities. Also taken into account in the etiology of diseases are environmental factors including pesticides, and atmospheric pollution.

The current practice in treating patients who suffer from abnormal organic conditions involve the use of drugs, radiotherapy and surgical intervention. Biofeedback and stress reduction is used to treat behavioral abnormalities.

The concern of the present invention is with treating patients having an abnormal condition which regardless of its cause and nature, is indicated by a depressed heart state characterized by a resting heart pulse rate that deviates from the normal resting rate and a maximum heart pulse rate that deviates from the normal maximum rate. The state is now referred to in medicine as a heart rate variability (HRV), that is reduced, the variability referring to the change in pulse rate from a minimum level at rest to a maximum level when energy is being expended.

Patient's who suffer from various diseases, such as multiple-sclerosis, cancer and cardiovascular disease, clinical depression, anorexia, and a host of other abnormalities, all exhibit a depressed heart condition and therefore a reduced heart rate variability. The extent to which the heart is depressed and impairs the patient's health varies from patient to patient. But it is this common denominator that is the foundation for an exercise program in accordance with the invention, whose objective is to lift this depression and restore the well being of the patient.

In my above-identified copending application there is disclosed a therapeutic exercise program for treating a patient having an abnormal condition indicated by a maximum heart pulse rate that deviates from a normal maximum rate and a resting heart pulse rate that deviates from a normal resting rate whereby the heart rate range is compromised, resulting in a reduced HRV.

The program is carried out by continuously monitoring the heart pulse rate of the patient while subjecting the patient to a series of exercise-relaxation cycles in which during each cycle the exercising patient first expends a surge of energy causing his pulse rate to reach a peak value above the resting heart rate to a degree that depends on the patient's physical state. At this point the patient relaxes and his heart rate, because of a pendulum effect induced in the patient's heart, swings down from the peak value to a point below said resting heart rate.

The exercise program is continued until the patient's HRV approaches a normal value and the abnormal condition is alleviated. While an exercise treatment as disclosed in my copending patent application is highly beneficial, it does not take into account the internal rhythms or waves of a biological clock and therefore does not take advantage of an exercise treatment that is so timed in related to these rhythms as to optimize the efficacy of the treatment.

SUMMARY OF INVENTION

In view of the foregoing, the main object of this invention is to provide a chronotherapy technique for treating a patient suffering from an abnormal condition reflected by a reduced heart rate variability (HRV), the treatment being adapted to expand HRV toward a variability state which in the patient being treated reflects a normal condition.

More particularly, an object of this invention is to provide a technique of the above type in which heart waves generated by a patient during an exercise session are synchronized in time with an internal wave of a biological clock in such a way as to expand the biological wave and thereby to enhance the efficacy of treatment.

A significant feature of a chronotherapy exercise technique in accordance with the invention is that it is addressed to a common denominator of human abnormality without regard to its cause, nature or origin, this denominator being a heart rate variability which is reduced and reflects an abnormal condition. The chronotherapy exercise technique by which the patient is treated is in harmony with his internal biological clock and is directed toward the recovery of an HRV that reflects a normal condition, the technique involving no chemotherapy, radiotherapy or any other know form of medical treatment or intervention.

Briefly stated, these objects are attained by a chronotherapy exercise technique for treating a patient whose abnormal condition, regardless of its nature or origin, is reflected by a heart rate variability (HRV) that is reduced and deviates from an HRV reflecting a normal condition. In this treatment, the patient in an exercise session undergoes a series of exercise-relaxation cycles in which during each cycle the pulse rate of the patient rises and then falls to produce a heart wave. To enhance the efficacy of the treatment, the heart waves generated in the course of an exercise session are synchronized in time with an internal wave produced by a biological clock, this activity inducing the HRV to cause it to approach an HRV reflecting, for the patient being treated, a normal condition.

BRIEF DESCRIPTION OF DRAWING

For a better understanding of the invention, as well as further features thereof, reference is made to the detailed description thereof to be read in connection with the annexed drawings wherein:

FIG. 1 is a block diagram of a system for carrying out a therapeutic exercise program in accordance with the invention;

FIG. 2 illustrates the heart wave of a patient undergoing a series of exercise-relaxation cycles in accordance with the program;

FIG. 3 illustrates the relationship between heart waves generated during exercise reasons and ultradian and circadian waves of a biological clock.

DESCRIPTION OF INVENTION

Wave Theory:

The theory underlying my invention is that interactions which take place in the human organism and involve the biochemistry of the organism and the behavior of its organs are based upon wave communication, not on the complexity of the structure itself.

In my invention we do not deal with multi-factorial structural phenomena from the bottom up and linear levels of measurement, for the invention is concerned with the use and shaping of wave activity as the ultimate cause and as a means to alleviate or cure organic and psychological disorders from the top down.

The present invention exploits the organization of lo individual behavior at the macro level, monitored and manipulated through the single concept of a heart wave to modulate and direct the behavioral wave patterns of many complex biochemical phenomena at the micro level. The invention recognizes that all forms of behavior are in fact wave behaviors. For example, the human organism has cycles or waves of behavior which expand energy and recover energy. The same is true for emotional stress and emotional recovery which is a wave of energy. This also applies to being awake or being asleep; or not eating and eating. All of these behaviors are waves of energy flux. The same concept of wave energy flux is true for all organ systems of the body and is especially obvious with the heart rate which is currently measured as an average linear rate over time. However, I have discovered this to be not a heart rate but a heart wave in which each heart beat entails a contraction/systole and relaxation/diastole which rises and falls over time to create wave motion of the heart beat. This I find to be a heart wave of energy flux.

The heart wave is unique in that it represents the connection and the window between different behavioral waves of the organism and its relationship to the environmental waves such as day/night cycles, climate cycles, etc., connecting these to the internal environment of molecular biological cellular/chemical/genetic oscillations, all manifesting behavioral waves of energy expenditure and recovery.

This present invention is based on the recognition that the waves produced by the heart are related not only to the behavioral waves of the human organisms which are cyclic in nature but also to molecular biological waves. All organ systems oscillate, and the heart produces a heart wave. All cells and genes undergo oscillation so that molecular biology is also a form of wave activity.

Wave activity occurs at the following hierarchical levels:

A. External Environment Waves
B. Human Organic Behavioral Waves
C. Heart Waves
D. Cell Waves
E. Gene Waves
F. Chemical Waves
G. Atomic Waves The above forms of wave activity all occur simultaneously within and across hierarchical levels. Any disorder at the biochemical level will therefore reflect change in the heart wave and in the behavior of the patient, whether it be behavioral disorders or organic disorders. The waves therefore represent the common denominator of simultaneous, coherent communications throughout the organism which is responsible for health and organization.

Wave shape is the key factor responsible for the flexibility and simultaneous coherent organization of all the chemistry, cells and of the various organ systems responsible for health, performance and longevity. This is an "action at a distance"

principle. From this perspective, all disease represents a disordered wave pattern in which the shape of the wave is distorted, giving rise to chemical imbalances where the timing is off and out of sync. The cure for diseases therefore is to correct, i.e., reshape the wave disorder by overriding or ablating the abnormal wave pattern, using the heart wave as the means to analyze and to bring into being over time, new heart wave patterns to prevent and reverse chronic disease or other abnormality.

I have found that the different cycles/waves of the different hierarchical levels of the human organism and its external environment are fractal shapes of one another. Fractal shaping means that communication is continuous and simultaneous across hierarchical levels. The fractal wave pattern shape is what determines the health versus chronic disease of the organism.

The present invention uses the heart wave as a means of diagnosing, monitoring and modulating to recreate normal one and one-half hour ultradian wave patterns which is then used to create the appropriate 24-hour cycle, this being used to create the appropriate monthly/lunar cycle, which is then used to create the yearly cycle and ultimately the lifetime cycle. It is not a matter of merely making or creating waves, for the actual shape of the wave is critical in terms of its flux from crest to through, i.e., amplitude and rate of change, i.e., acceleration and rate of recovery/deceleration.

The objective is to enhance the master heart wave reactivity and flexibility, its range/amplitude by appropriately integrating behavioral heart wave patterns monitored and analyzed by a computer. As the heart wave patterns are developed and changed over time toward normalcy, simultaneously the enormous complexity of biochemical interactions becomes more coherent to reverse chronic diseases or other abnormalities.

All wave behaviors including exercise and recovery, wakefulness and sleep, diet and eating, emotional arousal and relaxation, etc., are coherently organized and create the appropriate heart wave patterns. In particular, exercise and recovery are most important because of the ease with which one can create the cycles of energy expenditure and recovery.

The shape of the wave is novel and different from current patterns of behavioral approaches, i.e., relaxation, meditative techniques, aerobics, interval training, diets, all of which use prolonged linear behavioral approaches. In contrast, an exercise technique in accordance with the invention focuses in large measure on the spiking of wave patterns, i.e., short bursts of energy expenditure and recovery designed to increase the flexibility and range of heart waves. This is consistent with the examples hereafter given.

Spiking means the rate of acceleration and deceleration in the amplitude of the heart wave. The spiking heart waves are then developed as a set of cycles fractally shaped into an ultradian wave, sets of which are thereby fractally shaped into the 24-hour cycle pattern. This is then fractally shaped into the lunar monthly cycle, which is then fractally shaped into the yearly cycle, and is then fractally shaped into the life cycle. All of this is computer monitored so that the fractals can be analyzed for diagnostic and therapeutic purposes.

Examples of Wave Activity

1. The day/night cycle of the environment at the equator is sharply defined with minimal dawn and minimal dusk, i.e., a spike. It is known that chronic diseases, in particular depression, multiple sclerosis and more recently, as described in Newsweek, Jun. 7, 1993, in a report from the University of California, that cancers of the colon, prostate and breast are "virtually unknown" at the equator, and that with each rise in latitude, these diseases increase in incidence. I have found this to be so, because the day and night wave pattern becomes more linear, e.g. more dark/less light until one reaches the extreme northern or southern latitudes with virtually six months dark and six months light. Thus in the Lancet issue of Dec. 23,/30, 1989, in an article on page 1527 "Diabetes and Schizophrenia" it is noted that cold countries that are far from the equator have a preponderance of both diabetes and poor-outcome cases of schizophrenia.

2. Children when exercising exhibit extremely high heart rates up to 200 or more, but when they lie down, the heart rate then drops to the 80s. As we get older, it is known that our maximum heart rate declines progressively. I have found that the pattern of heart rate declines which are experienced with chronic diseases are indicative of these diseases.

3. Labor contractions at birth are cyclic. Work done at the Karolinska Institute in Sweden has shown that the cyclic contractions of the skull and brain of a baby when being born results in enormous outputs of various hormones, including adrenalin, etc., (with levels which only occur in later life with extreme exercise). These labor contractions were found to be responsible for an enhanced immune system, cardiovascular and respiratory functions, and neurophysiological behavior.

4. The hunting of animals in the wild is cyclic in nature, reflecting the spike to which I have referred. Thus in the article by O'Brien et al. "Search Strategies of Foraging Animals" in American scientist Vol. 78, on page 154 it is noted that in studies of the foraging behavior of fish, the search strategies are such that these fish "move in a relatively stop-and-go pattern." Animals in the wild rarely have chronic diseases. However, when placed in zoos or domesticated, the wave patterns are flattened and become less responsive, and the incidence of chronic diseases then rivals those of humans. It is also now generally recognized that chronic diseases and behavioral disorders, such as asthma, suicide, depression, drug addiction, criminal behavior and cancer are dramatically on the rise.

The Invention:

In a therapeutic exercise program in accordance with my invention, the program is tailored to treat a patient having an abnormal condition. This condition, regardless of its cause, nature and origin is indicated by a depressed heart state characterized by a resting heart pulse rate that deviates from a normal resting rate and a maximum or peak pulse rate obtained by physical exertion that deviate from the normal maximum rate.

At the outset of the program, the patient is tested to determine his initial heart pulse range extending between his resting and maximum heart pulse rates to provide a base line for the program. This initial range varies from patient to patient. Thus one patient may show an initial range whose maximum heart rate is 107 and whose resting heart rate is 51, while another may show an initial range going from a maximum of 130 down to 100. In both instances, the range is narrow and the heart is in a depressed state inducted by a heart rate variability that is reduced.

The purpose of the exercise program is to expand the range and flexibility and in doing so to relieve the patient of his or her abnormal condition.

FIG. 1 shows in block diagram the basic elements of a system for carrying out a program in accordance with the invention; the system including an exercise machine 10 which may be a stationary bicycle, a rowing machine or an other form of exercising apparatus suitable for a patient 11 having an abnormal condition. In practice, in lieu of an exercise machine, the patient may exercise by walking, running or jumping, or simply by arm and shoulder movements.

When machine 10 is operated by patient 11 who exerts himself, the heart beat of the patient 11 who exerts himself rises as a function of his exertion. Patient 11 is provided with a heart beat detector of any commercially available type which is coupled magnetically or by wireless means to a heart beat monitor 12 whose reading is presented on an electronic display 13. This display which is of the digital type is so placed that it can be read by the patient and the supervisor of the program.

Heart beat monitor 12 is coupled to a recorder 14 that graphically records and prints out the heart wave produced by the series of exercise-relaxation cycles the patient undergoes in the course of a session whose duration is controlled by the supervisor.

The output of recorder 14 digitalized and applied to a digital computer 15 in which the recordings produced in successive exercise sessions are stored and diagnosed to afford an analysis of the progressive changes taking place in the patient's condition and from which the computer can assign target numbers for future exercise cycles.

FIG. 2 graphically illustrates, in idealized form, the heart wave generated by the patient during successive exercise-relaxation cycles. The initial range of the patient, as determined at the outset of the program, is indicated in FIG. 2 by level P representing the maximum heart pulse rate the patient is able to then attain, and by level R representing his resting pulse rate. Because the patient suffers from an abnormal condition, regardless of its cause and nature, this initial range is the common denominator. Hence levels R and P are both deviate from normal, indicating a depressed heart state and a narrow heart wave range.

During each of the successive cycles, the patient operating the exercise machine or undergoing exercise is required to exert himself to produce a surge of energy giving rise to a rapid rise in pulse rate. The overall resting heart rate base line, after one to three exercise-relaxation cycles, will rise with successive cycles.

The first surge $S_1$ results in a maximum pulse rate $P_1$ that is somewhat above the initial maximum pulse rate line P. The patient, having attained peak $P_1$, then relaxes so that the pulse rate proceeds to drop sharply. But the pulse rate does not then drop to the initial resting level R, for the energy surge induces in the patient's heart a pendulum effect, causing the pulse rate to swing down to a resting rate $R_1$ which is below the initial resting rate level R.

A pendulum is a body suspended from a fixed support which is free to swing back and forth under the influence of gravity. The amplitude of the back and forth oscillation depends on the force of the actuating impulse which incites the pendulum into motion. If therefore at the end of an oscillation cycle, an impulse is applied causing the pendulum to swing forth to a greater degree than in the preceding cycle, it will then swing back to a greater degree.

We have found that the human heart behaves in a similar manner, and that a sudden surge of energy will cause the heart pulse rate to swing to a peak value, and resultant the down swing will cause the heart pulse rate to fall below its initial resting rate.

The spiked wave created by surge $S_1$ and the return swing $R_2$ represents the amplitude envelope of the varying heart pulse rate, for each point in the wave form represents a different pulse rate. Hence the envelope or the wave form reflects the varying repetition rates of frequencies of the heart beat.

In the next exercise-relaxation cycle, an energy surge $S_2$ produces a higher maximum pulse rate $P_2$ and a still lower resting rate $R_2$. And in the succeeding cycles produced by surges $S_3$ and $S_4$, still high maximum rates are produced. It is to be understood that from cycle to cycle, the peaks do not necessarily progressively increase, for a high peak may be succeeded by a lower peak.

Thus the successive exercise-relaxation cycles occurring in the course of an exercise session, act to expand the heart range of the patient. The temporal conditions under which the program is conducted (time of day, season, etc.) and its duration which may extend for several days, weeks or months, are such as to bring about a progressive increase in the maximum pulse rate attainable by the patient and so expand the heart wave range whereby at the conclusion of the program the patient's maximum heart pulse rate and his resting rate approach those of an individual free of the abnormal condition for which the patient was treated.

The cycles are best done at certain times of the day according to the body's internal physiological rhythms. I have found that unlike current thinking where exercise is believed to raise the immediate resting heart rate, that in fact a heretofore unknown phenomenon occurs in which a sudden rise in energy expenditure to a high heart rate will result in a pendulum effect, in other words, a lowering of the resting heart rate. The overall resting heart rate base line, after one to three exercise-relaxation cycles, will rise with successive cycles.

Computer technology makes it possible to analyze and compute the effects of the program for proposes of diagnosis and to determine the degree to which the patient is being restored to a healthy state. It is also useful to monitor wave fluctuations in temperature, blood pressure, EEG, EMG, etc. The heart wave patterns with chronic disorders is where the heart wave loses its responsivity and flexibility to rapidly reach high numbers and to rapidly recover. Thus with chronic disorders the heart wave assumes a relatively long wave length, a lower amplitude, a narrower range and decreased flexibility reflecting similar patterns of biochemical flux and similar behavioral patterns of a chronic, linear, repetitive nature. As pointed out by Ilya Prigogene, Nobel Laureate, fluctuations in wave patterns which go toward equilibrium and homogeneity result in molecular incoherence no matter how well organized and structured the molecules themselves are.

Shaping the Heart Wave:

An increase in the range of the heart wave resulting from the Program simultaneously enhances its flexibility. Shaping of the individual heart wave is effected by using exercise-recovery cycles, also by incorporating other behavioral waves of wakefulness and sleep, not eating and eating, and mental arousal and relaxation. Other techniques may be included, such as hot and cold showers, acupuncture, hyperthermia, and sun cycles, all forms of wave energy.

The appropriate shaping of the heart wave using the above modalities makes possible optimal fractal shaping of the following rhythms which enables the patient aid prevent and reverse disease:

a. the ultradian wave/1½ to 2 hours wave b. the circadian rhythm/24 hour wave c. the lunar monthly wave d. the yearly cycle Chronic diseases are characterized by:

1. Decreased range (lowered maximum amplitude and lowered resting pulse. Though some patients' heart rates are hyper-reactive, they eventually lower to subnormal levels as the Program proceeds and then the Program acts to raise the amplitude and flexibility as previously described.)

2. Decreased flexibility of the heart wave, i.e., slow response to any stressful perturbation or sometimes a hyper-active response to stress.

When the heart wave is "trained" or modulated through the Program to have an increased range and be more responsive, i.e., increased flexibility with a greater rate of change of acceleration and deceleration, we are then able to use the heart waves to shape the 24 hour cycles, and the monthly an yearly wave cycles which powerfully and simultaneously shape more responsive and coherent biochemical and genetic behavioral waves, thereby preventing and curing chronic diseases. It is the abnormal wave patterns of organism behavior and biochemical and genetic behaviors that are responsible for chronic diseases. These are restored to normal with the Program.

To exploit the underlying periodic components of the heart wave, one may use conventional digital signal processing (DSP) techniques for this purpose. The basis for these techniques lies in the solution of the Fourier Integral and its more prolific descendant, the Fast Fourier Transform (FFT).

Their applicability in heart wave analysis is as follows:

The first approach of interest is to uncover the natural, low and high frequency components present in the heart wave. Ideally, this should be done in the absence of any specifically prescribed regimen of cycles which would corrupt the basic nature of the "baseline." What is expected during this phase of analysis is a definite indication of natural periods on the order of minutes through days. The DSP technique employed for this measurement is commonly called "harmonic analysis." In harmonic analysis a fundamental (lowest) frequency is defined for a given data set, and higher frequency components are computed as real multiples of this fundamental. Note that phase as well as amplitude information is available.

The second approach to analysis involves treatment of specific pieces of the heart wave, specifically those pieces corresponding to commencement through cessation of cycles. These sections should be treated as discrete time signals, as opposed to continuous time signals. Analysis of this type of sinal differs from harmonic analysis in that the signal is not considered (i.e., assumed to be zero) outside of the defined limits. This approach will yield the specific frequency component "finger print" of any individual's heart wave cycle performance.

Taken together, these two approaches present the best available top level view of what is happening within the bio-system under analysis. Furthermore, through the accumulation of data sets on an individual, the specific monthly, yearly, etc., periodicities can be evaluated and shaped. Using this information, the physician can intelligently prescribe series and groups of cycles which re-enforce natural frequency components, negate undesirable components, and generally re-align and re-calibrate the individual's wave energy profile.

Examples of Treatment:

1. A 59-year-old patient with leukemia. Initial maximum heart rate was 107, resting heart rate was 51. After 8 months of modulating heart wave cycles with the Program, his heart rate maximum was 163, recovering down to low 60s, during which time his white cell count has been progressively dropping as much as 57,000 in the course of 2½ weeks.

2. A 24-year-old girl with anorexia. Maximum heart rate 150, resting heart rate in the mid to low 40s. After 5 months of the Program, her maximum heart rate reaches 190 and her resting heart rate recovering to the 60s. Anorexia resolved 100%.

3. A 30-year-old woman with multiple sclerosis whose maximum heart rate at onset was 120, with resting heart rates in the 40s. After treatment, the maximum heart rate reached 168, recovering down to the mid 50s. All symptoms of multiple sclerosis have cleared. Patient was able to get married.

4. A 28-year-old female with about an eight-year history of being HIV positive and active AIDS symptoms for about 1½ years, including severe diarrhea, severe depression and lethargy, weight loss of 20 pounds, monilia infections of the mouth, and total anergy of the immune system (no immune response with subdermal injections of candida) and facial rash. All symptoms disappeared between 1½ and 3 months of treatment, including the first immune response to candida injections in a year and a half. Heart wave patterns at onset ranged from 33 low heart rate to a hyperreactive maximum (which occasionally occurs as a "chaotic" response to stress) of 190, which during the Program her heart rates ranged to a maximum of 180 recovering into the mid 60s.

5. An 18-year-old male with a grad 3 to 4 malignant astrocytoma of the brain—6 to 7 months post-op was disoriented, sleeping 18 hours a day, short term memory deficit, etc. Heart range was maximum 120 recovering to 50s. After 2 years on the Program, the maximum was in the 170s down to the 60s and 70s, and after 3 years there has been no evidence of tumor recurrence.

6. A 55-year-old male with severe peripheral ischemia and neuropathy due to embolism in both legs. Post-amputation of left food, became severely addicted to Percodan narcotics for pain control and was refractory to medical treatment for suicidal depression. Heart waves ranged from the 100 maximum, down to 45 resting. After about 10 months on the Program his heart rates were 160 maximum, recovering down to the 60s. The depression cleared on the Program, his drug addictions disappeared, pain was relieved approximately 90% and he was able to go back to work.

7. A 28-year-old female with severe inflammatory disease of the bowel (Ileitis). Had previous surgery, was first seen by me when she was partially obstructed on a liquid diet, severe arthritis, unable to wear shoes and walking with great difficulty, and she also had erythema nodosum (an inflammatory disease of the skin) which was refractory to medical treatment including cortisone. She was to be placed on immunosuppressive therapy and surgery was planned at Mt. Sinai Hospital in New York. After one week on the Program, the inflammation subsided dramatically in the legs and she began to eat solid foods. After 3 months, all symptoms disappeared except for intermittent obstruction based on the mechanical scarring of the small intestine. At surgery, the involved intestine was removed, she is doing extremely well. Her initial heart rates were a resting heart rate of 100 to 110, with extreme hyperactivity on just standing to approximately 150. After the few months on the Program her resting heart rates were in the 60s with her maximum heart rate to 180.

8. A 65-year-old male with chronic viral hepatitis, whose initial heart rate maximum was 115 with recoveries down to the low 40s. After approximately one year on the program, his liver enzymes which were elevated returned close to normal. His depression, fatigue and weakness which made it difficult for him to leave his apartment, cleared and he was able to go back to skiing and playing tennis in a normal way. His heart rates ranged up to high 150s and recovered down to the 50s.

9. A 44-year-old male with severe chronic fatigue syndrome who was unable to work anymore. His heart rate range was 125 maximum, recovering down to the mid 40s. After 3 months on the Program his range is in the low 50s and maximum ins 170. H is chronic fatigue is about 80% improved and he has been able to return to work.

Improvements:

A therapeutic exercise program in accordance with the invention is particularly useful in treating patients exhibiting an abnormal condition reflected by a resting heart pulse rate that deviates from a normal resting rate for that patient and a maximum heart pulse rate that deviates from the normal maximum rate whereby the heart pulse rate range, the span from the minimum to be maximum pulse rates, is compromised.

The range is identified in medical literature as heart rate variability (HRV), it being known that in a patient whose HRV is reduced, this is symptomatic of an abnormal state without however indicating its cause, nature or origin. But the most significant aspect of a reduced HRV is that it represents a mortality risk.

Thus the article by Tsuji et al. in Circulation published by the American Heart Association (Vol. 20, No. 2—August 1994) is entitled "Reduced Heart Rate Variability and Mortality Risk in an Elderly Cohort—The Framinghan Heart Study". This article points out that HRV is influenced by various pathological factors, but regardless of the character of the pathology, a patient exhibiting a reduced HRV is at serious risk.

The same issue of Circulation carries an article by Moser et al. entitled "Heart Rate Variability as a Prognostic Tool in Cardiology." This article deals with the prognostic value of HRV "with respect to survival" and makes it evident that HRV is the key to mortality, for a patient whose HRV is seriously reduced is not likely to survive.

In the paper by Dardik published in Cycles—Vol. 43, No. 3, December 1996 entitled "The Origin of Disease and Health-Heart Waves" it is noted that a decrease in HRV emerges as "a single common risk factor for virtually all chronic diseases of all ages."

The objective of an exercise technique in accordance with the invention is to so treat a subject whose HRV is reduced as to induce his HRV to approach an HRV state that is normal for that subject, and in doing so to overcome whatever abnormality accounts for the reduced HRV.

To this end, in each session of treatment having a duration one half hour or whatever other period is appropriate to the existing condition of the patient, the patient is subjected to a series of exercise-relaxation cycles. In the course of each cycle, the exercising patient during the exercise phase of the cycle experiences a surge of energy, causing his monitored heart pulse rate to reach a peak rate above the resting pulse rate to an extent that depends on the patient's physical conditions. At this point, the patient in the remaining phase of the cycle then relaxes and, because of a pendulum effect, his heart pulse rate swings from the peak value to a minimum value below the resting pulse rate.

This pendulum effect plays a vital role in treatment, for the human heart behaves in the manner similar to that of an oscillating pendulum in which the amplitude of oscillation depends on the force of the impulse which incites the pendulum into motion.

In the course of each exercise-relaxation cycle, the heart pulse rate during the exercise phase rises to a peak level above the resting rate, while during the relaxation phase the pulse rate falls to a minimum level below the resting rate. This heart pulse rate which varies up and down during the time period covering the exercise-relaxation cycle produces a heart wave. The term heart wave, as used herein, is not the wave produced by the repetitive heart beat per minute, but the wave produced by the changing pulse rate of the heart in the course of an exercise-relaxation cycle which may last several minutes. If it takes say five minutes to produce a heart wave, and an exercise session lasts a half hour, then during this session six heart waves are produced, assuming a minimal break from cycle to cycle.

We have found that the efficacy of a therapeutic exercise program in accordance with the invention is significantly enhanced when heart waves generated during exercise sessions are synchronized in time with the waves or rhythms of the biological clock of the patient being treated. As noted in the article "Timing is Everything" by Hrushesky in The Sciences of July–August 1994, endogenous rhythms are innate in living systems. Such rhythms in sickness and in health are critical factors, "hence effective treatment must work with the biological clocks of the patient, not against them." As noted in Lancet 1997: 380-681–86 in an article by Levi et al.—Randomized multicentre trial of chronotherapy—"Chronotherapy was significantly less toxic and more effective than constantrate infusion. The results support the concept of temporal selectively of cancer chemotherapy."

These biological clocks govern one's pulse rate and blood pressure which markedly rise in the morning upon awakening. This biological timing may account for the high frequency of heart attacks and strokes at that time of day. Body temperatures also rise during the day and fall off sharply at night. And the secretion of hormones essential to the control of life processes rises and falls in the course of the day as determined by internal biological clocks.

Abnormalities associated with virtually every disease from arthritis to cancer are themselves organized cyclically. The treatment of illnesses in accordance with biological clocks is generally referred to as chronotherapy. Thus it is now the practice to schedule the administration of drugs to conform to biological rhythms, for whether a drug will be successfully absorbed by tissue cells or have an adverse effect may depend on the time of the day at which the drug is administered.

Thus in the article "Circadian-system Alterations During Cancer Processes" by Mormont et al. in the International Journal of Cancer 70-241–247 (1997) it is pointed out that chemotherapy for cancer is more effective when administered in a time schedule that takes into account circadian and ultradian rhythms.

Ultradian rhythms that govern physiological activities, such as pulse rate and blood pressure occur more than once every 24 hours. A single ultradian wave period takes from about 45 minutes to an hour on the upswing of the wave and about the same amount of time on the downswing. Hence the duration of an ultradian wave which occurs several times in every 24 hour period is about two hours.

A circadian wave which is more pronounced than an ultradian wave is a daily cycle, peaking only once every 24 hours. Infradian waves have periods longer than 24 hours. Thus there is a monthly cycle that follows the lunar calendar, this monthly wave peaking at the full moon. Monthly cycles govern hormonal activity, such as the secretion of estrogen which occurs on a monthly basis. The yearly wave is constituted by monthly waves and peaks at about September.

We have discovered that our therapeutic exercise technique based on exercise sessions during each of which a patient undergoes a series of exercise-relaxation cycles, that when the sessions are carried out in synchronism with the patient's biological clocks so as to properly expand ultradian, circadian and other biological rhythms, they are then measurably more efficacious than when exercise is conducted without regard to biological rhythms. Hence an improved exercise technique in accordance with the invention represents a new and highly significant form of chronotherapy, for it is effective against virtually all abnormalities.

A patient who suffers from a chronic disease and exhibits a reduced HRV, when subjected to an exercise-relaxation-cycle exercise session will at the outset of treatment generate in each cycle a Heart Wave that is narrowed. The reason for this is that the patient is then unable to raise his heart pulse rate to a peak level much above the resting pulse rate; hence the range running from a minimum pulse rate to this peak level is narrow.

The same patient who exhibits a narrowed Heart Wave also exhibits an ultradian wave whose range is narrowed, for when the heart is depressed so are the biological clocks. The human mechanism is not composed of discrete organs which operate independently of each other, for these organs communicate and interact with each other.

Hence the series of narrowed ultradian waves produced during a 24 hour period flatten out and merge with each other to define a narrowed circadian wave range. This in turn leads to a narrowed monthly wave. With chronic disease, the yearly wave is also flattened out to a lower and depressed level.

The shape and range of the heart wave representing the rise and fall of pulse rate in the course of an exercise-relaxation cycle is influenced by the biological clock, particularly the ultradian and circadian waves, for the heart pulse rate is governed by these waves. In addition, the proper scheduling of heart waves with respect to the biological waves will influence and determine the shape and range of these biological waves. Hence to optimize the beneficial effect of the cyclical exercise technique in which the patient generates heart waves, the timing of each session during which exercise is carried out is synchronized with an internal biological wave so to expand in the course of exercise both the heart wave and the biological waves including but not limited to ultradian, circadian monthly and life waves.

FIG. 3 illustrates a circadian wave C plotted on a time scale, the circadian wave C rising in amplitude to a peak $C_P$ at about 6 pm. Between 6 am and 6 pm three ultradian waves $U_1$, $U_2$ and $U_3$ are produced, the first taking place early in the morning, the second in the late morning and the third in the afternoon. Each ultradian wave U which lasts about two hours has a peak.

It will be seen in FIG. 3 that the exercise sessions are scheduled so that heart waves HW generated in each session are produced at a time which corresponds to the upswing of an ultradian wave U. Thus heart waves $HW_1$ of the first session are generated during the upswing of ultradian wave $U_1$, heart waves $HW_2$ of the next session, during the upswing of ultradian waves $U_2$, and heart waves $HW_3$ of the session which follows, during the upswing of ultradian waves $U_3$.

Heart waves HW are similar to those shown in FIG. 2 and therefore produce a pendulum effect, as previously described, so that with each successive exercise-relaxation cycle, the heart wave rises to a higher peak to expand the HRV. Because the scheduling is such as to place the Heart Waves at the upswing of the ultradian wave U to cause the ultradian wave to swing upwardly, this produces a pendulum effect in the downswing of the ultradian wave. This interplay of heart waves and ultradian waves acts to expand both the heart waves and the ultradian waves. The expanding ultradian waves $U_1$, $U_2$, $U_3$ in turn act to expand the daily circadian wave C.

In practice, the heart waves which are generated by a patient and the biological waves are computer analyzed to deliver the program by computer.

As noted in the Van Nostrand Scientific Encyclopedia 8th Edition in the section headed "Biological Timing and Rhythmicity" the biophysical and chemical basis for the operation of biological clocks has not yet been fully established, even though the pineal gland has been implicated. But what is known is that an interaction exists between the biological clock and the operation of the heart, for a reduced HRV has an adverse effect on the biological clock. Thus at a time when the biological clock commands an increase in heart pulse rate, a depressed heart condition resists this increase.

In a chronotherapeutic technique in accordance with the invention, the interaction between the heart and the internal biological clock is exploited by means of exercise-relaxation cycles producing a pendulum effect which overcomes the disorder responsible for a reduced HRV regardless of the nature of the disorder.

Though the invention has been described as a chronotherapy technique to improve the condition of a patient having an abnormality reflected by a reduced HRV, individuals more or less free of abnormality may benefit from the exercise technique which will serve to enhance their mental and physical well-being as well as to prevent the occurrence of a chronic disease.

While there has been shown and described preferred embodiments of the chronotherapy exercise technique in accordance with the invention, it will be appreciated that many changes may be made therein without departing from the spirit of the invention.

I claim:

1. A chronotherapy exercise technique for treating a patient having an abnormal condition reflected by a reduced heart rate variability which deviates from a heart rate variability reflecting a normal condition, the technique comprising the steps of:

A. continuously monitoring the heart pulse rate of the patient in the course of an exercise session during which the patient undergoes a series of exercise-relaxation cycles, the patient in an exercise phase of each cycle expending a surge of energy causing the pulse rate to rise to a peak rate above a resting rate, the pulse rate in a relaxation phase swinging down from the peak rate to a rate below the resting rate to produce a pendulum effect causing the pulse rate to rise to a higher peak rate in a succeeding cycle, the rising and falling pulse rate in the course of each cycle generating a heart wave; and B. sychronizing the time during which heart waves are generated with a wave of an internal biological clock whereby with repeated exercise sessions, the heart rate variability is induced to approach said normal variability.

2. A technique as set forth in claim 1, in which the wave is an ultradian wave.

3. A technique as set forth in claim 2, in which the synchronization is timed to cause the heart waves generated during the session to correspond in time to the upswing of the ultradian wave, thereby expanding the ultradian wave.

4. A technique as set forth in claim 1, in which the wave is a circadian wave.

5. A technique as set forth in claim 1, in which prior to the exercise session the heart rate variability of the patient is measured to determine the extent to which it is reduced, whereby the extent to which the session causes the heart rate variability to approach a normal variability can later be determined.

6. A technique as set forth in claim 1, in which said abnormal condition is a chronic disease, and said sessions are continued until the disease is substantially overcome.

7. A technique as set forth in claim 1, in which said abnormal condition is a behavioral disorder, and said sessions are continued until the disorder is substantially overcome.

8. A technique as set forth in claim 1, in which as the heart wave rate is monitored, a reading thereof is displayed.

9. A technique as set forth in claim 6, in which reading is recorded.

10. A technique as set forth in claim 3, in which the synchronization in times to cause the ultradian waves generate in successive sessions to correspond in time to the upswing of the circadian wave thereby expanding the circadian wave, the effect of which is to expand the heart wave and thereby induce heart rate variability to approach said normal variability.

11. A technique as set forth in claim 1, in which the heart waves and biological waves are analyzed in a computer in order to deliver a program by computer.

*12. A computer readable medium containing a program implementing a chronotherapy exercise technique for treating a patient having an abnormal condition reflected by a reduced heart rate variability which deviates from a heart rate variability reflecting a normal condition, the technique comprising:*

*A. continuously monitoring the heart pulse rate of the patient in the course of an exercise session during which the patient undergoes a series of exercise-relaxation cycles, the patient in an exercise phase of each cycle expending a surge of energy causing the pulse rate to rise to a peak rate above a resting rate, the pulse rate in a relaxation phase swinging down from the peak rate to a rate below the resting rate to produce a pendulum effect causing the pulse rate to rise to a higher peak rate in a succeeding cycle, the rising and falling pulse rate in the course of each cycle generating a heart wave; and*

*B. synchronizing the time during which heart waves are generated with a wave of an internal biological clock whereby with repeated exercise sessions, the heart rate variability is induced to approach said normal variability.*

*13. The computer readable medium of claim 12, in which the wave is an ultradian wave.*

*14. The computer readable medium of claim 13, in which the synchronization is timed to cause the heart waves generated during the session to correspond in time to the upswing of the ultradian wave, thereby expanding the ultradian wave.*

*15. The computer readable medium of claim 12, in which the wave is a circadian wave.*

*16. The computer readable medium of claim 12, in which prior to the exercise session the heart rate variability of the patient is measured to determine the extent to which it is reduced, whereby the extent to which the session causes the heart rate variability to approach a normal variability can later be determined.*

*17. The computer readable medium of claim 12, in which said abnormal condition is a chronic disease, and said sessions are continued until the disease is substantially overcome.*

*18. The computer readable medium of claim 12, in which said abnormal condition is a behavioral disorder, and said sessions are continued until the disorder is substantially overcome.*

*19. The computer readable medium of claim 12, in which as the heart wave rate is monitored, a reading thereof is displayed.*

*20. The computer readable medium of claim 17, in which reading is recorded.*

*21. The computer readable medium of claim 14, in which the synchronization in times to cause the ultradian waves generate in successive sessions to correspond in time to the upswing of the circadian wave thereby expanding the circadian wave, the effect of which is to expand the heart wave and thereby induce heart rate variability to approach said normal variability.*

*22. The computer readable medium of claim 12, in which the heart waves and biological waves are analyzed in a computer in order to deliver a program by computer.*

*23. A system for implementing a chronotherapy exercise technique for treating a patient, wherein said technique comprises subjecting said patient to a conditioning exercise session that itself comprises successive exercise-relaxation cycles, and wherein said patient has a heart pulse rate, a heart rate variability, and an abnormal condition indicated by a reduced heart rate variability that deviates from a normal heart rate variability reflecting a normal condition, said system comprising:*

*a heart beat monitor that monitors said heart pulse rate in the course of implementing said technique;*

*a heart beat rate display connected to said heart beat monitor, wherein said display displays said heart pulse rate; and*

*a computer connected to at least said heart beat monitor wherein said computer is programmed so that in the course of an exercise phase of each cycle the exercising patient expends a surge of energy causing his pulse rate to rise to a peak rate above a resting rate, the pulse rate in a relaxation phase to swing down from the peak rate to a rate below the resting rate to produce a pendulum effect causing the pulse rate to rise to a higher peak rate in a succeeding cycle, the rising and falling pulse rate in the course of each cycle generating a heart wave, and wherein said computer is programmed to synchronize the time during which heart waves are generated with a wave of an internal biological clock whereby with repeated exercise sessions, the heart rate variability is induced to approach said normal variability.*

*24. The system of claim 23, in which the wave is an ultradian wave.*

*25. The system of claim 24, in which the synchronization is timed to cause the heart waves generated during the session to correspond in time to the upswing of the ultradian wave, thereby expanding the ultradian wave.*

*26. The system of claim 23, in which the wave is a circadian wave.*

*27. The system of claim 23, in which prior to the exercise session the heart rate variability of the patient is measured to determine the extent to which it is reduced, whereby the extent to which the session causes the heart rate variability to approach a normal variability can later be determined.*

*28. The system of claim 23, in which said abnormal condition is a chronic disease, and said sessions are continued until the disease is substantially overcome.*

*29. The system of claim 23, in which said abnormal condition is a behavioral disorder, and said sessions are continued until the disorder is substantially overcome.*

*30. The system of claim 23, in which as the heart wave rate is monitored, a reading thereof is displayed.*

*31. The system of claim 28, in which reading is recorded.*

*32. The system of claim 25, in which the synchronization in times to cause the ultradian waves generate in successive sessions to correspond in time to the upswing of the circadian wave thereby expanding the circadian wave, the effect of which is to expand the heart wave and thereby induce heart rate variability to approach said normal variability.*

*33. The system of claim 23, in which the heart waves and biological waves are analyzed in a computer in order to deliver a program by computer.*

* * * * *